United States Patent [19]

Webler

[11] Patent Number: 4,819,655

[45] Date of Patent: Apr. 11, 1989

[54] INJECTATELESS THERMAL CARDIAC OUTPUT DETERMINATION METHOD AND APPARATUS

[76] Inventor: William E. Webler, 151 Seaspray South, Laguna Niguel, Calif. 92677

[21] Appl. No.: 81,352

[22] Filed: Aug. 4, 1987

[51] Int. Cl.$^4$ .............................................. A61B 5/02
[52] U.S. Cl. .................................................. 128/713
[58] Field of Search ............... 128/713, 720, 724, 725, 128/736, 303.12, 400, 401; 604/43; 73/204

[56] References Cited

U.S. PATENT DOCUMENTS

| | | | |
|---|---|---|---|
| 2,982,132 | 5/1961 | Mendolowitz | 128/691 |
| 4,059,982 | 11/1977 | Bowman | 73/204 |
| 4,111,209 | 9/1978 | Wolvek et al. | 128/401 |
| 4,476,877 | 10/1984 | Baker | 128/736 |
| 4,569,355 | 2/1986 | Bitterly | 128/691 |
| 4,632,125 | 12/1986 | Webler | 128/713 |
| 4,662,383 | 5/1987 | Sogawa et al. | 128/401 |
| 4,671,295 | 6/1987 | Abrams et al. | 128/713 |
| 4,674,518 | 6/1987 | Salo | 128/713 |

Primary Examiner—Francis Jaworski
Assistant Examiner—George Manuel
Attorney, Agent, or Firm—Lyon & Lyon

[57] ABSTRACT

The method and system use a catheter that is configured such that a fluid may circulate within it. With the catheter in position, the fluid may circulate down one lumen as far as the RA or RV, over to another lumen and back up and out of the catheter. Nothing is injected into the bloodstream. On this or another catheter, a temperature sensor is positioned in the PA to monitor mixed venous blood temperature. Temperature sensor devices monitor the fluid temperature at the inlet to and outlet from the catheter. The flowrate of fluid circulation is controlled at a known value or monitored. The circulating fluid is preferably cooled to near ice temperature prior to input into the catheter. This fluid temperature and flow rate are preferably held relatively constant.

Soon after fluid circulation is initiated a relatively steady state heat transfer system is attained. The circulating fluid cools the blood through the lumen walls. It also cools any adjacent fluid lumens which also cool the blood through their lumen walls and through dilution, if the lumen is used to introduce an IV solution. An appropriate heat balance equation allows cardiac output to be calculated. After an appropriate amount of data is collected, fluid circulation is discontinued, allowing the system to re-equilibrate. Once equilibrium is reestablished, another measurement cycle may be initiated.

8 Claims, 6 Drawing Sheets

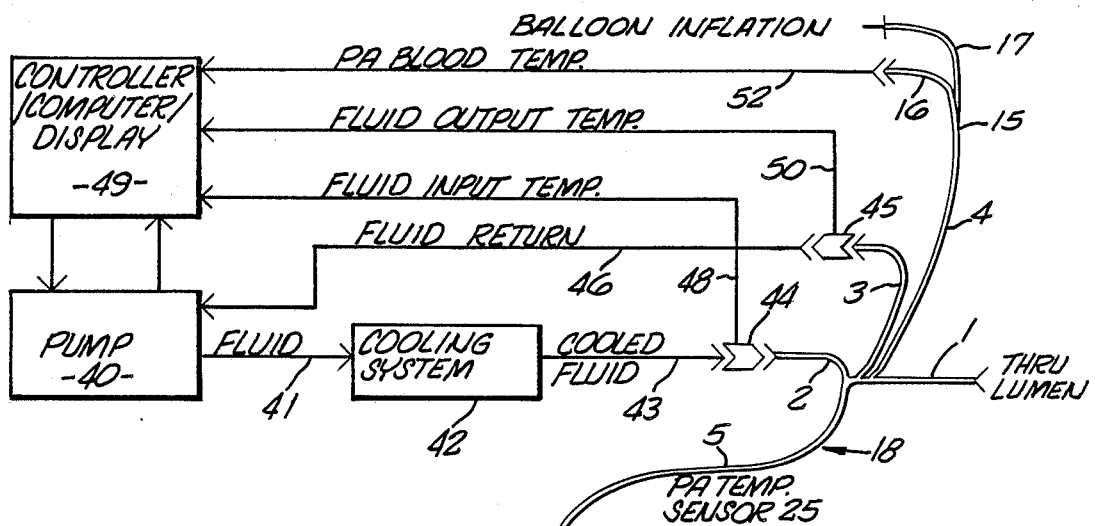
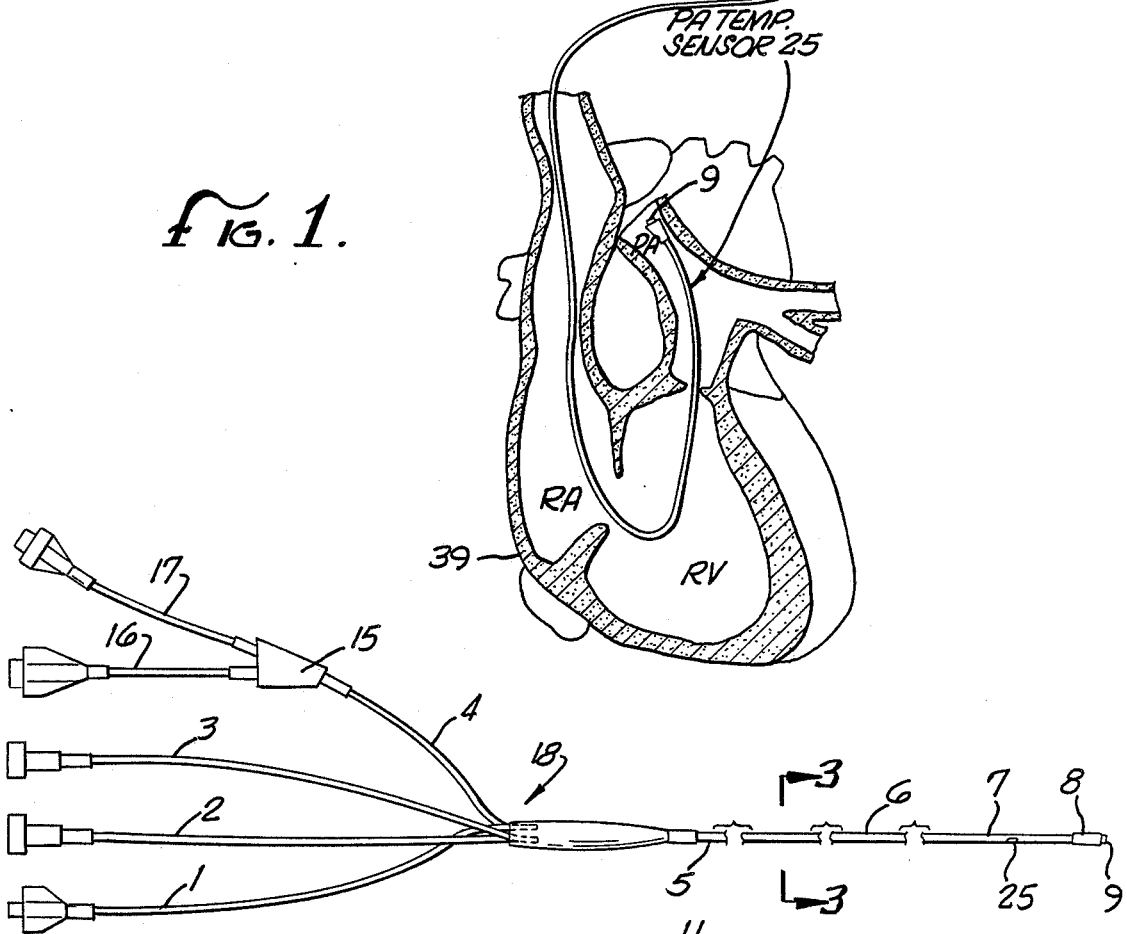
fig. 1.
fig. 2.
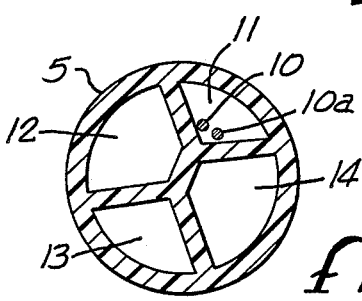
fig. 3.

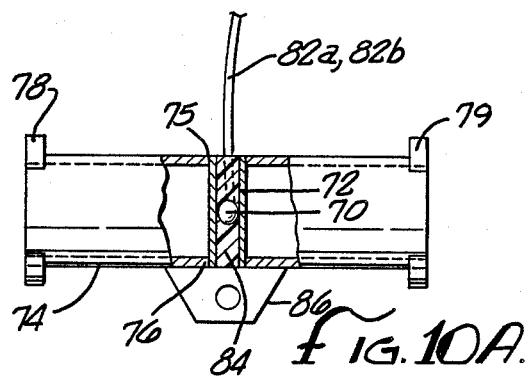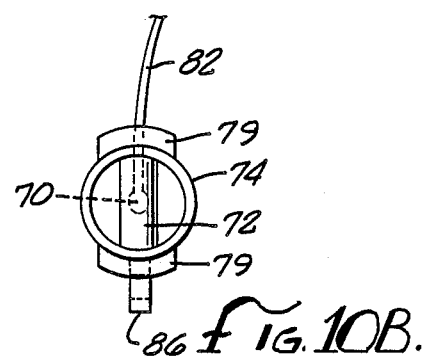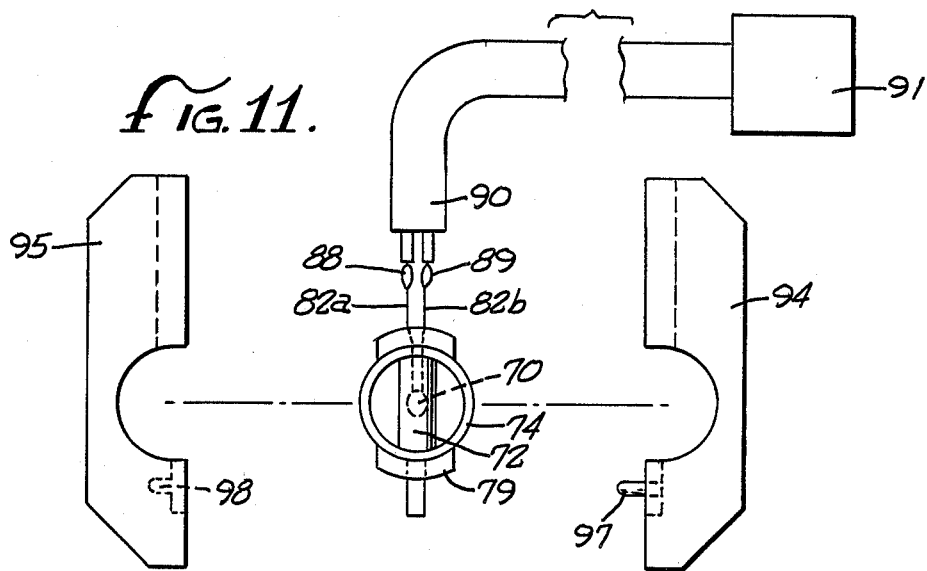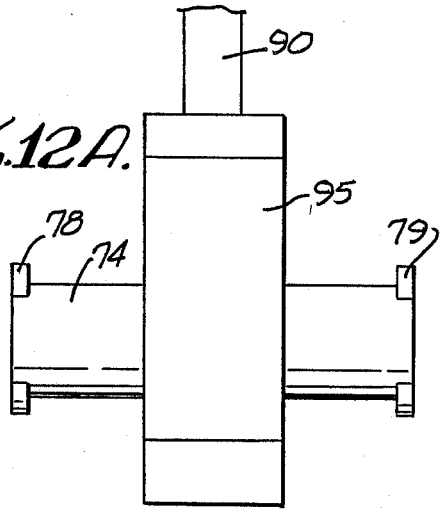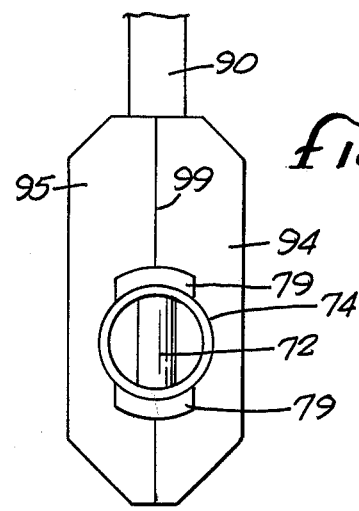

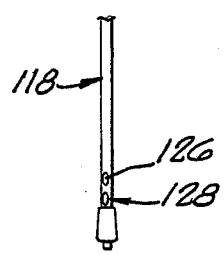
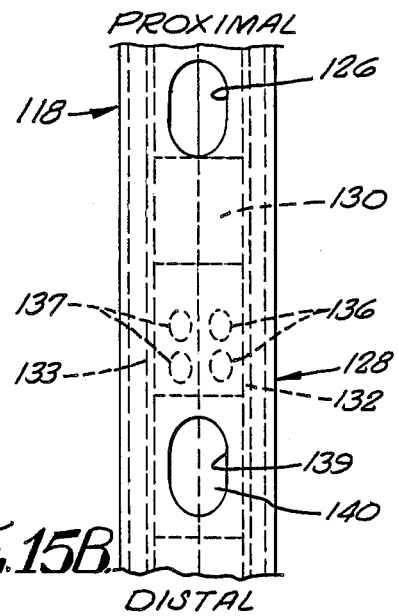
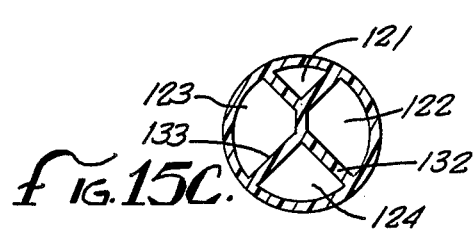
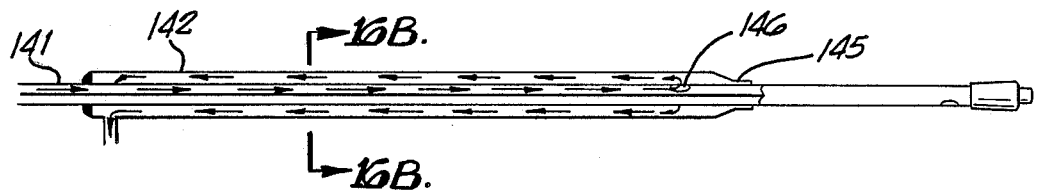
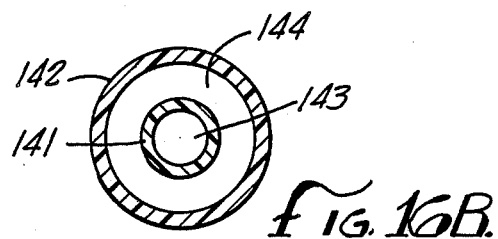

INJECTATELESS THERMAL CARDIAC OUTPUT DETERMINATION METHOD AND APPARATUS

BACKGROUND OF THE INVENTION

This invention relates to measuring cardiac output and, more particularly, to a method and means of continuously measuring cardiac output.

Many medical procedures include the monitoring of cardiac output (the rate of blood flow through the heart). A widely used method is to place a catheter into the right side of the heart through a major vein to position a temperature sensor, such as a thermistor, in the pulmonary artery. This catheter may also be placed to perform other functions such as pressure monitoring. To determine cardiac output, a fluid cooler than the blood, usually a glucose or saline solution, is injected down one of the lumens in the catheter and into the bloodstream in the vicinity of the right atrium. This results in a thermodilution temperature curve being sensed in the pulmonary artery by the thermistor. By controlling the volume and temperature of the injected fluid, recording the blood temperature prior to the thermodilution curve and integrating the thermodilution curve over time, an attached computer is able to calculate and display the cardiac output. Because these curves are of short duration, and the blood flow is subject to longer term variations, conventional practice is to take several measurements and average them. Reference may be made to U.s. Pat. No. 4,632,125, the disclosure of which is incorporated herein.

Unfortunately, the foregoing procedures result in a significant volume of fluid being injected into the patient's bloodstream. To prevent stressing the patient's system in a condition commonly referred to as "volume loaded," the frequency of cardiac output determinations must be limited. Many physicians and researchers desire to have much more frequent determinations to provide better patient care or more complete research data.

In addition, particular care must be taken that the injected fluid is sterile to avoid microorganism related problems being introduced into the patient. Since the injections are commonly made by syringe, the connection to the injectate lumen of the catheter must be broken and reconnected to the next syringe for the next injection. Often these syringes are prefilled and placed in an ice bath prior to use. Despite extreme attention to good sterile procedure, these operations still present a finite risk of contamination. To respond to this risk, some catheter manufacturers have introduced systems which allow the use of a single syringe, and cool the fluid in a heat exchanger prior to its being routed to the syringe. These systems have not gained wide acceptance for a variety of reasons. Chief among them are, the clumsiness of such systems, accuracy questions due to the lack of control of the injectable temperature and its monitoring, and the difficulty of maintaining the sterility of the inner surface of the syringe.

Other dilution techniques using indicators such as cardio-green dye suffer from the same kind of problems. In addition, they suffer from a recirculation of the indicator that complicates the procedure and also limits the acceptable rate at which determinations of cardiac output may be made. This accounts for their lack of popularity.

To eliminate these problems, many systems have been proposed, but only a few have met with even limited success. Completely non-invasive ultrasonic techniques are available, but require expensive equipment and skilled operators. Also the required placements of external devices on the patient preclude their use during some surgical procedures or in the case where the patient may move during a determination. The electromagnetic flow meter technique has been incorporated into a catheter to eliminate the previously required surgical procedures to implant and remove the necessary sensor. However, the present size of the sensor on the catheter precludes the use of the popular "sterile sheath" systems of catheter insertion. Thus a cut-down must be performed, at a greater risk to the patient. Also, current design does not allow useful and desired pressure monitoring to be done. In addition, they are intended for reuse, which requires hospital cleaning and sterilization procedures and facilities that are often not feasible. Other catheter mounted velocity sensor systems have suffered from many design and theoretical problems that have not been resolved. Although they potentially can greatly reduce the sterility risks and dramatically increase the frequency that cardiac output determinations may be made, no system has yet been introduced.

SUMMARY OF THE INVENTION

According to the concepts of the present invention, a catheter with a distal temperature sensor (thermistor) is positioned in the pulmonary artery (PA). Cooled (or heated) fluid is circulated down one catheter lumen and back up an adjacent lumen and out of the catheter. Nothing is injected into the bloodstream. The fluid may circulate as far as the right atrium (RA) or upper right ventricle (RV). The blood flowing near and adjacent the catheter is cooled (or heated) by the circulating fluid by heat transfer through the lumen walls of the catheter. The cooled (or warmed) blood is mixed with other incoming blood in the RV and ejected into the PA by the heart. The rate of heat gained (or lost) by the circulating fluid is calculated by monitoring the temperature of the fluid entering and exiting the catheter and controlling or monitoring the flow rate of the fluid. After a short time to cool (or heat) the catheter and adjacent tissues, the rate of heat gained (or lost) by the circulating fluid will be equal to the rate of heat lost (or gained) by the blood. By sensing the blood temperature change in the PA, the cardiac output may be calculated. A constant "C" is incorporated into the calculations to account for the differences in heat capacities of the blood and fluid, as well as heat gained (or lost) from sources other than the blood. A further analysis and heat balance equation will be provided subsequently.

The following sets forth advantages of the present continuously updatable cardiac output (CUCO) system:

1. Each measurement represents an average value.

2. A measurement cycle may be completed within the time usually taken to do a conventional thermodilution cardiac output (TDCO) series.

3. The system is a true closed loop system; that is, the circulating fluid never comes in contact with the patient. Thus the risk of introducing microorganisms directly into the bloodstream is greatly reduced, if not eliminated entirely.

4. A system employing appropriate subsystems to monitor the pressure required to circulate the fluid and to ensure that all fluid sent down the catheter is returned, can be virtually failsafe. This allows preprogrammed automatic measurement cycles without an operator present. The data can be stored for later retrieval or logged into a central system automatically.

5. No new technology need be developed to implement the system on a commercial basis.

6. Other catheter functions can be retained.

7. Measurement cycles may be repeated continuously. Any tendency to lower the patient's blood/body temperature, if not desired, is easily negated by the use of the heating pads commonly available and in widespread use in all hospitals.

8. Conventional catheter insertion procedures and accessories are applicable.

Accordingly, it is an object of the present invention to provide an improved method and apparatus for measuring cardiac output.

Another object of this invention is to provide a continuously updatable cardiac output (CUCO).

A further object of this invention is to provide a closed loop system for enabling continuously updatable cardiac output to be provided.

Another object of this invention is to provide a new form of catheter.

These and other objects and features of the present invention will become better understood through a consideration of the preceding and following description, taken in conjunction with the drawings in which FIG. 1 is an exemplary system block diagram illustrating the concepts of the present invention;

FIG. 2 is a plan view of a single catheter apparatus according to the present invention;

FIG. 3 is an enlarged cross-sectional view along lines 3—3 of FIG. 2;

FIGS. 10a–12b are enlarged assembly diagrams of input and output fluid temperature sensor devices used in the systems of FIG. 1 or FIG. 7;

FIGS. 15a–15c illustrate and improved and preferred form of dual catheter apparatus; and FIGS. 16a–16b illustrate another form of catheter employing concentric tubes.

DETAILED DESCRIPTION

Figure 4:
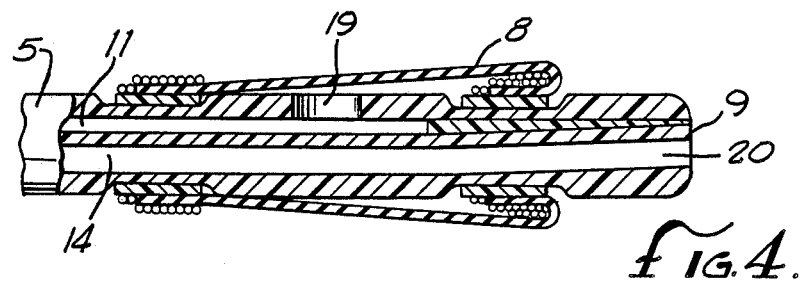
FIG. 4 is an enlarged partial axial sectional view of the distal tip of the catheter of FIG. 3.

Turning now to the drawings, and first to FIGS. 1 and 2, a single catheter apparatus 18 is shown which comprises a catheter tube 5 having a balloon inflation/thermistor wire run lumen 11 (FIG. 3), a through lumen 14, a thermistor mounting lumen 12 and a lumen 13. The lumens 12 and 13 are used as fluid input and fluid output lumens, respectively, as will be discussed in more detail later. A pressure monitoring tube 1 (FIGS. 1 and 2), a fluid input tube 2, a fluid output tube 3 and extension tube 4 are fused at the proximal end of the catheter tube 5 within the respective through lumen 14, fluid input/thermistor mounting lumen 12, fluid output lumen 13 and balloon inflation/thermistor wire run lumen 11.

The catheter tube 5 may be extruded from a suitable biocompatible plastic material as is well known. The catheter tube 5 is flexible, elongated and sized to be received through a vein into the heart. The catheter tube has a proximal end where the tubes 1, 2, 3 and 4 are fused within its lumens 14, 12, 13 and 11, respectively, and a distal end 9. The balloon inflation/thermistor wire run lumen 11 extends continuously from the proximal end of a balloon inflation tube 17 through a "Y" connector 15, the extension tube 4 and a port 10 (FIG. 4) to a balloon 8, which is closely adjacent to the distal end 9. The balloon 8 and the manner in which it is inflated through the balloon inflation/thermistor wire run lumen 11 are conventional.

Figure 5:
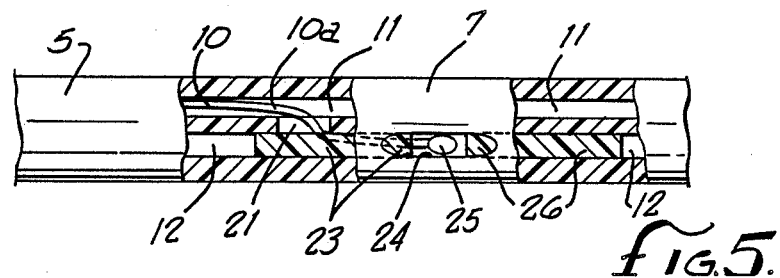
FIG. 5 is an enlarged partial axial sectional view of a thermistor mount and thermistor wire crossover to a balloon inflation/thermistor wire run lumen of the catheter.

The catheter 18 includes a thermistor mounting assembly 7 which is located approximately one and six tenths inches from the distal end 9 in the fluid input/thermistor mounting lumen 12. The assembly comprises a distal plug 16 (FIG. 5), an access slot 24, a thermistor 15, and a proximal plug 23 within the lumen 12. The electrical leads 10, 10a of the thermistor 15 are routed under the proximal plug 23, through a cross-over hole 21 into the balloon inflation/thermistor wire run lumen 11 proximally, through the extension tube 4, through the "Y" connector 15 and into the thermistor connector tube 16. A flexible insulating adhesive holds the assembly 7 together and provides an air-tight seal for the cross-over hole 21. The manner in which the thermistor 25 is mounted within the catheter 18 and the electrical leads routed is conventional.

The through lumen 14 extends continuously from the proximal end of the pressure monitoring tube 1 to the distal end 9 where it opens at a distal port 20 (FIG. 4). The through lumen 14 can be used, for example, to monitor pressures within the patient.

Figure 6:
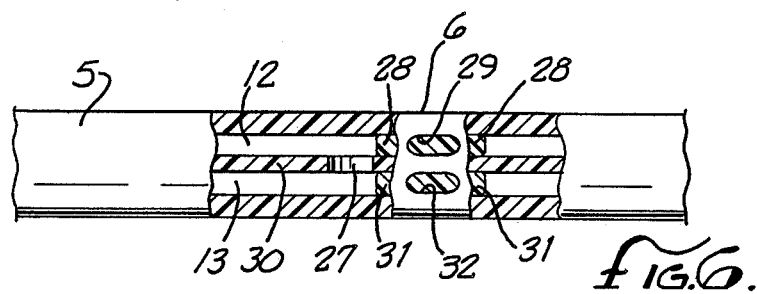
FIG. 6 is an enlarged partial axial sectional view of the fluid circulation assembly of the catheter of FIG. 3.

According to an exemplary embodiment of the present invention, catheter 18 includes a fluid circulation assembly 6 which is located approximately nine inches from the distal end 9 to allow cooled (or heated) fluid to circulate in a flow path confined within the catheter. The assembly 6 comprises an access slot 29 (FIG. 6) cut in the external wall of the fluid input/thermistor mounting lumen 12 and a plug 28 within this lumen 12, an access slot 32 in the external wall of the fluid output lumen 13 and a plug 31 within this lumen 13, and a circulation hole 27 cut through the common wall separating the two adajcent lumens 12, 13. A flexible adhesive holds the plugs 28,31 in place, sealing the lumens 12, 13 from fluid flow distally down the lumens 12, 13 or out the access slots 29, 32. This construction creates a continuous closed fluid path from the proximal end of the fluid input tube 2, through the fluid input/thermistor mounting lumen 12, through the circulation hole 27, and through the fluid output lumen 13 to the proximal end of the fluid output tube 3. Of course, the fluid may be circulated in either direction, and other assemblies and/or lumens can be provided, if desired, to provide additional functions for the catheter. The method of construction of the fluid circulation assembly 6 will be discussed later. The inlet and outlet lumens (e.g., 12, 13) may be adjacent as shown or not adjacent (do not share a common wall).

FIG. 1 illustrates the catheter 18 disposed in the heart 39 in the manner described briefly earlier and as will be described in more detail subsequently. A suitable pump 40 supplies fluid through tube 41 to a cooling (or heating) system 42 which adjusts the temperature (cools or heats) the fluid, and the cooled (or heated) fluid is applied through a tube 43 and a temperature sensor 44 to fluid inlet tube 2. The return fluid tube 3 is connected through a temperature sensor 45 and a tube 46 to the pump 40 for recirculation through the catheter. The fluid inlet temperature sensor cable 48 connects the fluid input temperature sensor 44 to a controller/computer/display 49. Fluid outlet temperature sensor 45 is similarly connected via a cable 50 to a controller 49. Similarly, the thermistor 25 is electrically connected through the thermistor connector tube 16 and a cable 52 to the controller 49.

As will be apparent to those skilled in the art, the pump 40 functions to provide a constant fluid flow rate at a given value or provide a signal indicative of the flow rate value upon command. It also can include means for detecting fluid flow anomalies (e.g., over-/under pressure, fluid loss, pump function, and the like) and provide an indicative signal to the controller 49. The pump 40 can be a piston or tube pinching type operated at a constant speed or pressure and with a flowrate signal. The pumping chamber may be integral to the pump or part of another assembly (e.g., cassette or modular type).

The cooling system 42 operates to cool the input fluid, and it may comprise a conventional refrigeration system or ice bath and a heat exchanger. The heat exchanger can be part of another assembly if desired. In some designs, a small circulation pump and connections for a cooling jacket for the fluid line can be beneficial.

The controller/computer/display typically includes a conventional microprocessor, LCD display, selector switch and/or membrane pushbutton assembly, and it performs various functions as will be readily apparent to those skilled in the art. It monitors and stores PA blood temperature, fluid input temperature, fluid output temperature, and depending on the particular design, fluid flow rate. It will be apparent to those skilled in the art that fluid flow rate can be controlled by controlling the operation of the pump 40 which has known operating parameters (e.g., a constant volume per cycle). The controller functions to turn the pump 40 on and off and to monitor its functional status. The controller can allow the operator to choose and initiate a TDCO determination cycle, a TDCO/RHEF determination cycle, a CUCO determination cycle, a CUCO cycle to determine the constant "C," or continuous CUCO cycles at a given interval. It allows the operator to input a constant for TDCO determinations, a constant for CUCO detemations, the interval between continuous CUCO determinations, and the assumed cardiac output to be used for constant "C" detemation. It can indicate to the operator when a determination cycle is in progress and when the system is ready for the operator to choose and initiate a determination cycle. It can compute and store the constant "C," CUCO, TDCO, RHEF as appropriate for the initiated determination cycle. The controller allows the operator to choose the parameter to be displayed-TDCO (up to last five), CUCO (last five manually initiated cycles and all automatically initiated cycles), RHEF (up to last five), the current value of "C," or current PA, fluid input or fluid output temperature. It can indicate to the operator the nature of any detected faults. It can shut down the pump and alert the operator if a leak or other problem is detected during a CUCO cycle. The controller provides electrical connections to the pump, catheter thermistor, fluid input temperature sensor and the fluid output temperature sensor.

A simplified heat balance equation, further comments concerning the present exemplary embodiment and a sample calculation are set forth below.

Simplified Heat Balance Equation and Notes:

CO = Cardiac Output (L/min), calculated $T_B$ = Baseline Blood Temperature (°C.), a measured (by thermistor 25) average prior to circulating the fluid. A time equal to one or two respiratory cycles is ideal for averaging.

$T_B'$ = Blood Temperature (measured by thermistor 25) after stabilization of circulating fluid rate of heat gain (or loss) (°C.), a measured average* done in the same manner as $T_B$.

$T_I$ = Circulating Fluid Temperature (measured by 44) at the input to the catheter (°C.). Depending upon system configuration this may be a measured average* or an assumed or controlled value.

$T_O$ = Circulating Fluid Temperature (measured by 45) at the exit from the catheter (°C.), a measured average* obtained at the same time as $T_B'$.

$\dot{V}_I$ = Circulating Fluid Flow Rate (L/Min), a system controlled constant for best results (measured by 49 control of 40).

C = Calculation Constant, determined in vitro/in vivo.

*Measured over the same time period/interval.

$$\Delta T_B = |T_B - T_B'| \qquad \Delta T_I = |T_I - T_O|$$

$$(CO)(\Delta T_B) C = \dot{V}_I (\Delta T_I)$$

$$CO = \frac{\dot{V}_I (\Delta T_I)}{C (\Delta T_B)}$$

1. This system is expected to induce temperature variations in the PA that are tied to the respiratory cycle. Thus these variations will be periodic at the respiratory rate. Running the $T_B'$ data through a Fourier or similar transform will yield the period and amplitude of this cycle. If the amplitude of the variation is significant then the best results will be obtained by using the period or multiples of it as the interval over which to process the recorded data.

2. Due to the volume of blood surrounding the catheter and the RV mixing volume, a delay and a capacitive (RC) type response will be present in the $T_B'$ data once fluid circulation has begun. Thus introducing a delay between the $T_B'$ data used and the $T_I$ data used will improve results. Also including $T_B'$ data on each side of the chosen interval for the duration of this delay or some part of it in order to compute the average will improve results. One simple method to generate a suitable delay period is to use the interval between the initiation of fluid circulation and the change in blood temperature ($\Delta T_B$) exceeding a certain level above that induced by respiratory variations.

3. Due to the volume of the circulating fluid in the catheter between the $T_I$ and $T_O$ temperature sensors (44, 45) a response similar to the blood temperature data can be expected in the $T_O$ data. Thus handling the data in a similar manner to determine the $T_O$ average will improve results. A simple method to determine a suitable delay is to divide that volume by $\dot{V}_I$. If $\dot{V}_I$ is a constant, then this value is solely dependent upon the catheter specifications, and most likely will have little significant variation. Thus the system may treat this delay as a constant.

4. For best results, $T_I$ and $\dot{V}_I$ should be as constant as practical.

5. The constant "C" is experimentally determined on a flow bench and confirmed in animal experiments. A constant flow/temperature bench with proper attention to temperature, insertion length, dead volume and mixing volume will yield best results. The in vivo confirmations can be obtained most easily by using the system catheter PA temperature sensor for bracketing TDCO determinations. TDCO injections may be made with a separate short catheter inserted at another site. All of this data will also be very useful in testing the many possible algorithm approaches and variations.

6. The time required for system stabilization may be an experimentally determined constant long enough to cover the worst case. To allow a more rapid determination, it may be calculated by the system. One simple method is to begin recording data when the change in $\Delta T_I$ has been below a certain level for a set period of time.

7. For patient comfort, maintenance of catheter physical properties and heat transfer rate considerations, a cooled circulating fluid will yield the best results.

8. The system will be relatively immune to errors induced by IV infusions, provided that the infustion rate and temperature are held constant.

9. Due to the nature of the system, any flow down the through lumen into the PA must be shut off prior to and during a CUCO determination to avoid errors.

10. It is likely that a factor must be included into the $T_B'$ determination to offset resistance changes in the temperature sensor leads caused by catheter temperature changes where they are run.

The following is a sample calculation:

$$C = 1.00 \quad \dot{V}_I = 2 \text{ cc/sec } (.12 \text{ L/min})$$
$$T_I = 3° \text{ C.} \quad T_O = 12° \text{ C.} \quad \Delta T_B = .20$$
$$CO = \frac{(.12)\, 9}{(1)(.20)} = 5.4 \text{ L/min.}$$

In order to enable a further understanding of the present concepts, the events in a measurement cycle are:

1. Initiation of a measurement either manually or as part of an automatic cycle pre-programmed earlier.
2. Cease collecting and monitoring $T_B$ data.
3. Begin circulating the fluid in the catheter 18.
4. Monitor $T_I$, $T_O$ and $T_B'$ data.
5. When relative equilibrium is detected, begin recording $T_I$ data.
6. Begin recording $T_O$ data.
7. Begin recording $T_B'$ data.
8. Cease recording $T_I$ data.
9. Cease recording $T_O$ data.
10. Cease circulating the fluid in the catheter.
11. Cease recording $T_B'$ data.
12. Process the data and compute cardiac output.
13. Monitor and process $T_B$ to determine when temperature stability is regained, $T_B$ data recording may begin, and another measurement cycle may be initiated.

The construction and assembly of the input and output flow temperature sensors 44 and 45 are illustrated in FIGS. 10 through 12. Both of the sensor assemblies 44 and 45 can be identical and constructed as shown. Each of the temperature sensors as shown in FIGS. 10a–10b comprises a thermistor 70 disposed in a stainless steel tube 72 which, in turn, is mounted in a stainless steel tube 74 having a through hole 75, 76 for receiving the tube 72. The tube 74 has Luer fittings 78 and 79 at the ends thereof. Wires 82a,b from the thermistor 70 extend out of the tube 72, and the thermistor is secured and insulated within the tube 72 by electrically insulating potting compound 84. The tube 74 has secured thereto a stainless steel locking flange 86.

The wires 82a,b from the thermistor 70 are connected and welded at 88, 89 to the conductors of a dual conductor cable 90 as shown in FIG. 11. A suitable electrical connector 91 is attached to the end of the cable 90. A suitable insulating adhesive (not shown) preferably covers the welds 88, 89 of the thermistor wires 82a, 82b.

The temperature sensor assembly further includes a plastic holder comprising a male section 94 and a female section 95 as seen in FIGS. 11 and 12. This holder 94, 95 provides thermal insulation for the thermistor assembly (tubes 72, 74) and strain relief for the cable 90. A suitable locking pin 97 and pin receptacle 98 are provided in the respective sections 94, 95. A suitable adhesive is used to hold together the plastic holder sections 94 and 95 where they are joined together as indicated at 99. The basic construction methods are conventional, and the stainless steel parts are welded watertight as is well known to those skilled in the art.

Figure 13A:
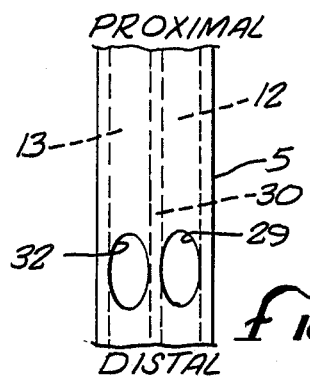
FIGS. 13a–13f illustrate the method of modifying a conventional catheter to allow closed loop fluid circulation according to the present invention.
Figure 13C:
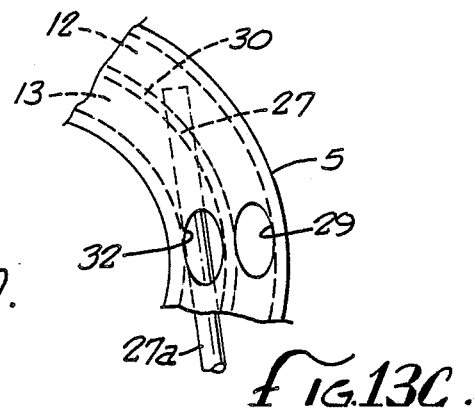
Figure 13B:
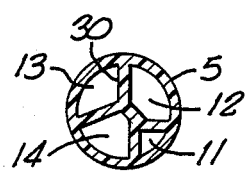
Figure 13D:
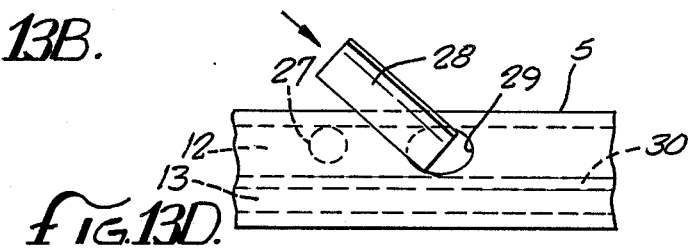
Figure 13E:
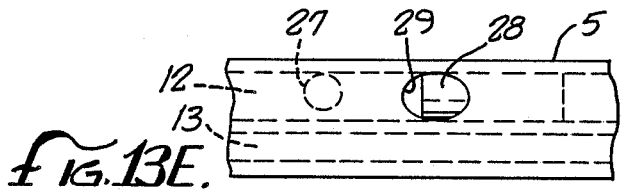
Figure 13F:
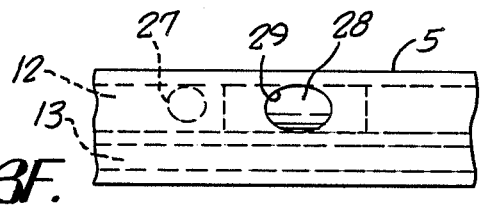

Turning now to the details of construction of the fluid circulation assembly 6 (FIG. 13), the same is constructed by first cutting the two adjacent access slots 29, 32 through the external walls of the adjacent lumens 12, 13. These access slots 29,32 should be just large enough to allow the respective appropriate plug 28, 31 to be pushed through them and into the respective lumens 12, 13 without permanent deformation of the slots 29, 32. The method used to cut the slots is conventional. Next the circulation hole 27 is cut, as proximally from the access slots 29, 32 as practical, through the common wall 30 separating the adjacent lumens 12, 13. The sharpened end of a small tube 27a is inserted through a slot 32 from distal to proximal directions as seen in FIG. 13c at an angle such that the sharpened end of the tube 27a encounters the lumen wall 30 between the adjacent lumens as proximally as practical from the slot 32. Bending the catheter 5 in the direction of the side that the slot is on is helpful (FIG. 13c). A blunted syringe needle with its edges sharpened is ideal as the tube 27a for this purpose. By gently pressing the tube 27a into the lumen wall 30 while rotating the tube, a hole may be made in the wall between the adjacent lumens. This procedure may be repeated through either slot 29, 32 to enlarge the hole or add other holes as required. Next the two plugs 28, 31 are cut out of a suitable non-toxic plastic material, such as PVC. The cross-section of each plug should be similar to that of the lumen in which it will reside in order to insure proper sealing. The plugs 28, 31 should be at least ¼" longer than the longest dimension of the access slot through which it will be inserted in order to allow sufficient length for sealing the access slots 29, 32. A plug is installed by first dipping one end of it in a suitable uncured flexible adhesive, such as urethane epoxy, then inserting that end of the plug distally as seen in FIG. 13D, away from the circulation hole 27, through the appropriate access slot (29 in this case) into the associated lumen until the entire plug is within that lumen, but the proximal end of the plug is still visible and accessible through the access slot. The uncured adhesive will act as a lubricant during this process to increase the ease of assembly. Next the adhesive is applied to the exposed proximal end of the plug in the lumen through the access slot. Then the plug is moved proximally within the lumen until the access slot is well sealed, as seen in FIG. 13f, but the circulation hole 27 is still unobstructed. The plug may be moved by sticking it with a pin through the distal end of the access hole (e.g., 29) and then moving both the pin and the plug proximally until the pin encounters the proximal end of the access slot. Several repetitions of this process may be necessary. Finally the adhesive is applied within the access slot onto the plug and inside edges of the access slot. The adhesive will wick to fill any unfilled gaps around the plug and also adhere to the inside edges of the access slot to give the catheter surface a smooth feel and insure a proper seal. Reapplication or removal of excess adhesive may be necessary prior to the adhesive curing.

DUAL CATHETER CONTINUOUSLY UPDATABLE CARDIAC OUTPUT

Figure 7:
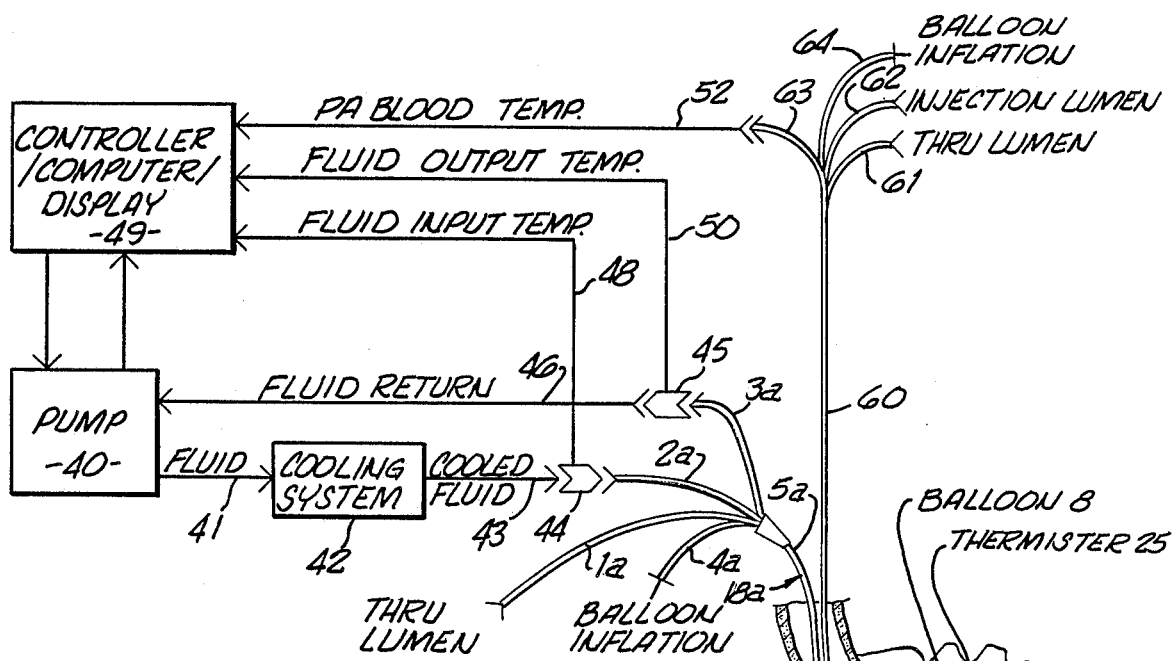
FIG. 7 is a system block diagram of a dual catheter system according to the present invention.

In this system variation a conventional TDCO capable catheter 60 is positioned in the PA in the normal manner (note FIG. 7). Any conventional catheter which contains a temperature sensor that is positioned in the PA may be used. Then a special shorter catheter 18a according to the present invention is inserted at another site. This catheter incorporates a flow directing balloon, two lumens for the circulating fluid, and a through lumen for pressure monitoring (to insure proper positioning) or infusion. The catheter 18a is shorter because it is designed to be inserted no further than the RV and then withdrawn into the RA. Both catheters are shown in FIG. 7 inserted through the superior vena cava. One or both may be inserted through the inferior vena cava if desired. The conventional catheter PA temperature sensor is used for either conventional TDCO/RHEF data collection or in conjunction with the special catheter for continuously updatable cardiac output. The pump, cooling system temperature measuring system and associated components are the same as in the single catheter system, the only difference being in the catheters themselves.

In this system, continuous patency infusion down the through lumen of the conventional catheter need not be discontinued before and during a CUCO determination. Also drug/IV infusions down the through lumen of the special catheter may be continued regardless of CUCO determinations as long as their rate and temperature is not altered before or during the determination. In fact, an IV drip down this lumen will result in a larger $\Delta T_B$ and $\Delta T_I$ being generated with a corresponding increase in CO accuracy. In this system, TDCO's may be used to generate the constant "C" internally to achieve a higher degree of system accuracy. The versatility and increased accuracy of such a system may out-weigh the inconvenience and expense of a second insertion in many cases or in research applications.

Figure 8:
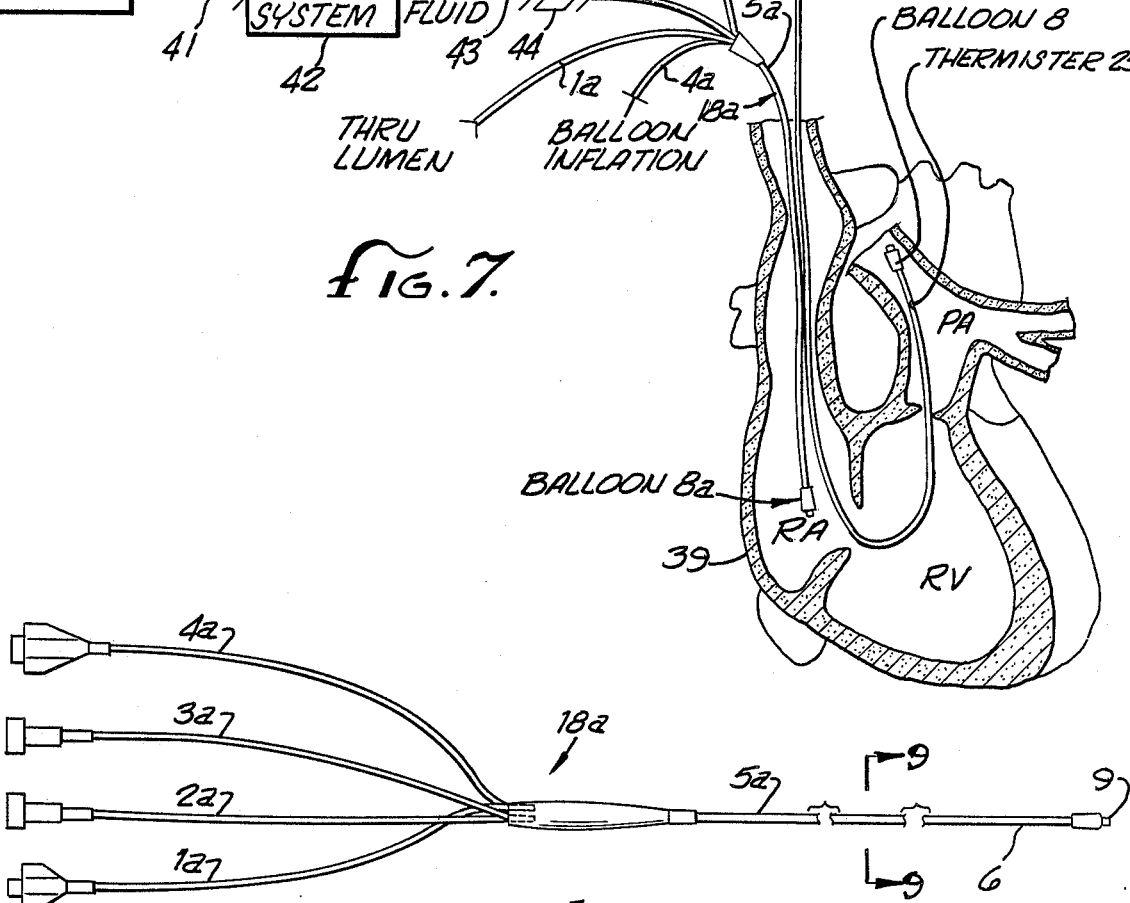
FIG. 8 is a plan view of a dual catheter apparatus for use in the system of FIG. 7.
Figure 9:
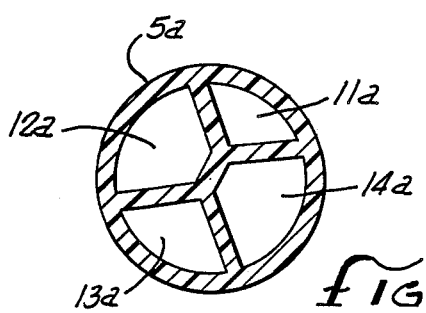
FIG. 9 is an enlarged cross-sectional view along a line 9—9 of FIG. 8 of the catheter and its lumens.

The catheter 18a of the dual catheter apparatus shown in FIG. 7 is illustrated in further detail in FIGS. 8 and 9 and comprises a catheter 18a with a tube 5a having a balloon inflation lumen 11a (FIG. 9), a through lumen 14a, a fluid input lumen 12a and a fluid output lumen 13a. A pressure monitoring tube 1a, a fluid input tube 2a, a fluid output tube 3a and a balloon inflation tube 4a are fused to the proximal end of the catheter tube 5a within respectively the through lumen 14a, the fluid input lumen 12a, the fluid output lumen 13a and the balloon inflation lumen 11a.

As discussed earlier, the catheter tube 5a may be extruded from a suitable biocompatible plastic material, and it is flexible, elongated and sized to be received through a vein into the heart. The catheter tube 5a has a proximal end (where the outer tubes 1a, 2a, 3a and 4a are fused within its lumens 14a, 12a, 13a and 11a, respectively) and a distal end 9. The balloon inflation lumen 11a extends continuously from the proximal end of the balloon inflation tube 4a through a port to the balloon which is closely adjacent to the distal end 9 in the same manner that lumen 11 of FIG. 4 communicates through port 19 to balloon 8 adjacent the distal end 9. The balloon 8 and the manner in which it is inflated through the balloon inflation lumen 11a are conventional.

The through lumen 14a extends continuously from the proximal end of the pressure monitoring tube 1a to the distal end 9 where it opens at the distal port 20 (FIG. 4). The through lumen 14a can be used, for example, to monitor pressures within the patient to facilitate positioning or for fluid infusion once in position.

According to the present invention, the catheter 18a includes a fluid circulation assembly 6 which is located approximately one and six tenths inches from the distal end 9. The assembly 6 is the same as previously described with reference to FIG. 6.

Turning again to the heat balance equation, a further, more complex model and extension of the simplified model analysis discussed earlier is set forth below. The actual cooling fluid temperature that enters that portion of the catheter which is in contact with the blood is referred to $T_I'$. As is known, a part of the catheter assembly (as seen in FIG. 1 or FIG. 7) is outside of the body in the ambient air, normally at 25° C., and that part of the catheter within the heart is at the temperature of the blood, normally at 37° C. Additionally, in the analysis below $H_F$ represents the heat gained by the fluid from the blood and $H_B$ represents the heat lost by the blood to the fluid.

$$T_I + C(25 - T_I) = T_I'$$

$$C = \text{a constant } 0 < C < 1$$

Actual fluid return temperature as it leaves that portion of the catheter which is in contact with the blood is $T_O'$.

$$T_O' + C(25 - T_O') = T_O$$

"C" is the same if the two extension tubes and lumens (2, 3 and 12, 13) are nearly the same materially and dimensionally.

$$T_O' + 25C - CT_O' = T_O \qquad \Delta T_F = T_O' - T_I'$$

$$T_O'(1 - C) = T_O - 25C \qquad \Delta T_F = \text{actual temperature increase of the fluid due to the blood.}$$

$$T_O' = \frac{T_O - 25C}{1 - C}$$

$$\Delta T_F + \frac{T_O - 25C}{1 - C} - T_I - 25C + CT_I$$

-continued $$\Delta T_F = \frac{T_O - 25C}{1 - C} - T_I(1 - C) - 25C$$

$$H_f = \Delta T_F V_I \quad H_B \frac{\Delta T_B (CO)}{1.06} \quad H_B = H_F$$

$$\frac{\Delta T_B(CO)}{1.08} = \Delta T_F V_I \rightarrow CO = \frac{\Delta T_F \dot{V}_I (1.06)}{\Delta T_B}$$

Figure 14A:
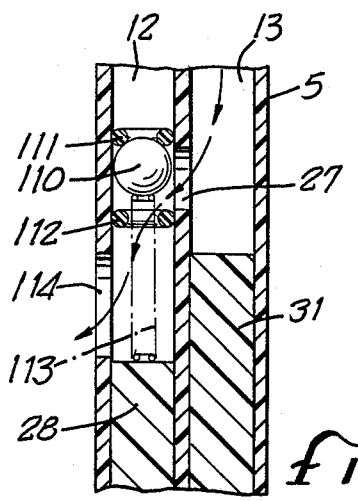
FIGS. 14a–14b illustrate catheter modifications for allowing infusion using a closed loop circulation lumen.
Figure 14B:
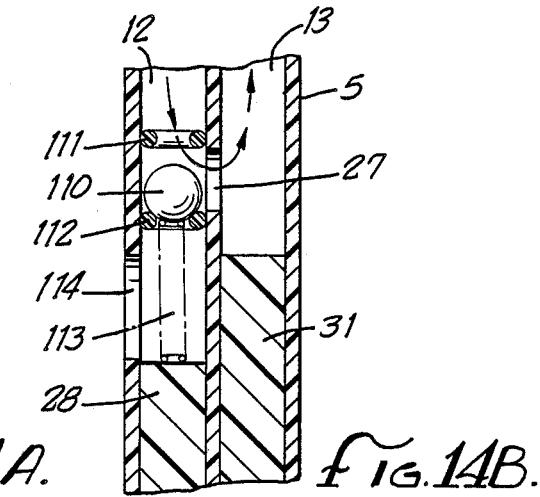

FIGS. 14a and 14b illustrate a modification of a fluid circulation assembly 6 (note FIG. 6 also) for allowing infusion as well as the closed loop circulation between lumens 12 and 13. In this modification, a ball check valve comprising a ball 110, two seats 111, 112 and biasing means 113 (such as a spring) and an outlet port 114 are added as shown in FIG. 14A. The plugs 28 and 31 are arranged in the lumens 12 and 13 as shown in FIG. 14. The ball check valve assembly is disposed with respect to the circulation hole 27 so that if infusion fluid is applied through lumen 13, the ball 110 will move to the position shown in FIG. 14a (upward as shown) so that the infusion liquid can pass through the hole 27, past the ball 110 and seat 112 and through the outlet port 114. In the normal circulation mode, the fluid is fed into the lumen 12, and it passes through the hole 27 and returns through the lumen 13. In this case, the pressure and flow of the fluid in the lumen 12 through the hole 27 maintains the ball 110 against the seat 112 so as to effectively seal the infusion port 114.

FIGS. 15a through 15c illustrate an improved and perferred form of dual catheter apparatus 118 and method of construction. The construction is similar to that shown in FIG. 6, except the tip of the catheter 118 is formed as illustrated in FIG. 15a and the tubes are rearranged into the lumens as illustrated in FIG. 15. The lumens as seen in the cross-sectional view of FIG. 15c include a balloon inflation lumen 121, a fluid input lumen 122, a fluid return lumen 123 and a pressure monitoring/infusion lumen 124. The improved catheter 118 includes an exit port 126 for the pressure monitoring/infusion lumen 124 and which is cut in the external wall of lumen 124. The catheter 118 includes a fluid circulation assembly 128 which is shown in greater detail in FIG. 15b.

The fluid circulation assembly 128 as seen in FIG. 15b includes a plug 130 inserted into and secured in the lumen 124 by a suitable adhesive so as to seal the distal end of lumen 124. This figure illustrates in dashed lines a wall 132 between the lumens 122 and 124, and a wall 133 between the lumens 123 and 124. Holes 136 are shown as cut in the wall 132 separating the lumens 122 and 124, and holes 137 are shown cut in the wall 133 between the lumens 123 and 124. An access hole 139 is cut in the external wall of lumen 124 to allow the other holes to be cut, and it is plugged with a plug 140 and sealed with an adhesive.

As will be apparent, lumens 122 and 123, which are the fluid circulation lumens, are sealed distal to the sets of holes during the tip forming and balloon assembly process. With the arrangement as shown in FIG. 15, the IV drip (infusion) down lumen 124 will be more rapidly cooled since there are now two walls (132, 133) through which cooling can take place, and this will result in higher signal levels ($\Delta T_B$, $\Delta T_I$).

FIG. 16 illustrates another form of catheter according to the present invention by which higher signal levels may be obtained. This catheter design incorporates an inner tube 141 which provides a fluid input lumen 143 and a concentric or coaxial outer tube 142. The torodial space between the tubes 141 and 142 provides a lumen 144 which serves as the return or output lumen. The fluid input lumen 143 includes a port 146 just proximal to a fusion point 145 which communicates with the return lumen 144. The inner tube 141 may extend distally further than the outer tube is fused (at 145) to it and also can contain an additional lumen or lumens (not shown) for injection, infusion, pressure monitoring, temperature sensing, balloon inflation and so on which are accomplished distally from the fusion point 145. Thus, at least one lumen 143 of the inner tube 140 is used to convey the cooled fluid down the inner tube distally where it flows through the port 146 into the space between the inner tube 140 and outer tube 141 and which space forms the return lumen 144. The fluid then flows proximally in the lumen 144 and back up the catheter and out at a suitable fitting to the temperature sensor like the sensor 45 of FIG. 1. As will be apparent, the input fluid flows through a temperature sensor like sensor 44 of FIG. 1.

Although the cooling system 42 is shown in FIGS. 1 and 7 in the fluid input line, it can be placed in either the fluid input or return lines. It is desirable that the fluid lines be insulated. If a cassette or other modular type pump is used for 40, a disposable portion which contains the fluid lines, a heat exchanger, access for filling with fluid, connections for the fluid temperature sensors, and the cassette or modular pumping chamber may be manufactured and marketed as a separate assembly. Additionally, a compliance chamber may also be desirable.

In order to provide a further understanding of the concepts of the present invention, set forth below is a heat transfer model which models the heat transfer characteristics of a catheter inserted into a flowing bloodstream.

$\dot{Q}$ = heat lost by the blood to the fluid per second (cal/sec) $\lambda$ = heat conductivity of the catheter walls ((cal/sec)/°C.·cm)

A = heat transfer surface area (cm²)

$\Delta T$ = temperature differential across the heat transfer surface (°C.)

$\Delta X$ = thickness of the heat transfer area.

Assumptions/Constants 7.5F Catheter OD=0.100″=0.254 cm, $\Delta X$=0.010″=0.0254 cm 85 cm insertion length, 45 cm effective heat transfer length $\dot{V}$ = fluid circulation rate = 2 cm³/sec $T_I$ = fluid input temperature = 3° C.

$\lambda = 5 \times 10^{-4}$ (CAl/sec)/°C.·cm (value for rubber used)

$T_B$ = Surface temperature of the catheter is at blood temperature = 37° C.

$T_C$ = inside temperature of the catheter, one half the sum of $T_I + T_O$ $T_O$ = fluid output temperature 75% of the catheters OD participates in heat transfer Equations/Heat Transfer Estimates/Implications $$\dot{Q} = \frac{\lambda A \Delta T}{\Delta X}$$

$$\Delta T = \left( 37° C. - 3° C. - \frac{\dot{Q}}{2\dot{V}} \right) = \left( 34 - \frac{\dot{Q}}{4} \right)$$

-continued $$\Delta x = .0254 \text{ cm}$$

$$A = \pi(.254)(45)(.75) = 26.9 \text{ cm}^2$$

$$\dot{Q} = \frac{(5 \times 10^{-4})(26.9)(34 - \dot{Q}/4)}{.0254} = .53(34 - \dot{Q}/4)$$

$$1.132 \dot{Q} = 18$$

$$\dot{Q} = 15.9 \text{ cal/sec}$$

(1) Using a more heat conductive material (larger λ) is the most fertile area to increase signal ($\Delta T_B$)).

(2) Thinner catheter walls (smaller $\Delta X$) is the next most fertile.

(3) A larger OD catheter or increasing the fluid circulation rate ($\dot{V}$) will also increase signal ($\Delta T_B$).

(4) The antecubital or femoral insertion site will yield an increased signal over the jugular site.

System Results (1) $\Delta T_I$ will be approximately 7.95° C.

(2) At 3 L/min blood temperature will change ~0.337° C. At 5 L/min blood temperature will change ~0.202° C. At 7 L/min blood temperature will change ~0.144° C.

Although exemplary embodiments of the invention have been shown and described, various changes, modifications and substitutions may be made without departing from the spirit and scope of this invention, and the same are intended to be encompassed within the scope and spirit of the appended claims.

What is claimed is:

1. A method of providing injectateless thermal cardiac output determinations comprising the steps of
    inserting a catheter into a heart cavity, the catheter having temperature measuring means for measuring blood temperature within the heart, and the catheter including lumen means for providing a closed loop flow of a fluid through the catheter into and out of the heart and confined within the catheter,
    adjusting the temperature of the fluid, measuring the temperature of the fluid prior to entering the catheter, and supplying the temperature adjusted fluid to the catheter and thus into the vicinity of the heart,
    measuring the temperature of the fluid returned from the vicinity of the heart by the catheter,
    measuring the flow rate of the fluid, and
    calculating cardiac output based on the temperature of the fluid entering and exiting the catheter, flow rate of the fluid, and change in blood temperature.

2. A method as in claim 1 wherein
    the temperature of said fluid is adjusted by cooling the fluid to a temperature below the temperature of blood in the body, and
    said fluid is directed into a catheter having first and second lumens, with the fluid directed into the first lumen and exiting from the second lumen, there being a cross-over path between said first and second lumens within a portion of the catheter disposed within the vicinity of the heart.

3. A method as in claim wherein
    said temperature of the fluid is adjusted by cooling the fluid, and
    the cardiac output is calculated by determining the rate of heat gained by the fluid flowing through the catheter.

4. A method of providing injectateless thermal cardiac output determinations comprising the steps of
    providing a confined flow of fluid within but not in direct contact with the bloodstream to develop a heat exchange between the fluid and the blood, and
    measuring the heat exchange rate between the fluid and the blood, and measuring the temperature change of the blood, and determining therefrom the cardiac output.

5. A method as in claim 4 wherein
    the fluid is circulated within lumen means of a catheter placed in the bloodstream, the temperature of the blood in the distal vicinity of the catheter is measured by temperature sensing means, and the temperature of the fluid is measured both entering the catheter and exiting the catheter.

6. A catheter "sized to be inserted into an artery or vein" for use in providing injectateless thermal cardiac output determinations comprising lumen means for enabling an enclosed closed loop flow of fluid within the lumen means of the catheter when placed in a bloodstream, said lumen means comprising first and second lumens within the catheter and a cross-over hole between the lumens in a portion of the catheter to be disposed in the bloodstream to enable the fluid to flow onto one of said lumens, through the cross-over hole and back out of the catheter through the other of said lumens.

7. A catheter as in claim 6 comprising first and second concentrally arranged tubes one spaced inside another and each having a wall, the inside tube providing the first lumen and at least a portion of the space between said tubes providing the second lumen, said cross-over hole comprising a distal opening in the wall of the inside tube.

8. A method of providing injectateless thermal cardiac output determinations comprising the steps of
    providing a confined flow of fluid within but not in direct contact with the bloodstream to develop a heat exchange between the fluid and the blood, the fluid being circulated within lumen means of a catheter placed in the bloodstream, said lumen means comprising first and second lumens providing a closed loop flow of said fluid through the catheter into and out of a heart and confined within the catheter, and
    measuring the heat exchange rate between the fluid and the blood, and measuring the temperature change of the blood, and detrmining therefrom the cardiac output.

* * * * *